(12) United States Patent
Mueller et al.

(10) Patent No.: US 6,806,966 B1
(45) Date of Patent: Oct. 19, 2004

(54) COPPER CMP FLATNESS MONITOR USING GRAZING INCIDENCE INTERFEROMETRY

(75) Inventors: Dieter Mueller, Cupertino, CA (US); George Kren, Los Altos Hills, CA (US); Cedric Affentauschegg, San Jose, CA (US)

(73) Assignee: KLA-Tencor Techologies Corporation, Milpitas, CA (US)

( * ) Notice: Subject to any disclaimer, the term of this patent is extended or adjusted under 35 U.S.C. 154(b) by 379 days.

(21) Appl. No.: 09/693,614

(22) Filed: Oct. 20, 2000

Related U.S. Application Data

(63) Continuation-in-part of application No. 08/930,378, filed as application No. PCT/EP96/03381 on Aug. 1, 1996, now Pat. No. 6,100,977.

(30) Foreign Application Priority Data

Jan. 24, 1996 (DE) ......................................... 196 02 445

(51) Int. Cl.[7] ................................................. G01B 9/02
(52) U.S. Cl. ...................................................... 356/514
(58) Field of Search ............................. 356/514, 513, 356/512, 511, 521, 488, 494

(56) References Cited

U.S. PATENT DOCUMENTS 4,030,830 A * 6/1977 Holly ......................... 356/489
6,100,977 A   8/2000 Muller
6,249,351 B1  6/2001 de Groot
6,271,925 B1  8/2001 Muller
6,414,752 B1 * 7/2002 Sullivan et al. .......... 356/237.5

FOREIGN PATENT DOCUMENTS

DE       261422      5/1987
DE     19511926     10/1996

OTHER PUBLICATIONS

Peter de Groot, "Diffractive grazing–incidence interferometer," *Applied Optics*, Apr. 2000, vol. 39, No. 10, pp. 1527–1530.
John Wallace, "Symmetry improves interferometer," Laser Focus World, Jul. 2000, pp. 24–28.

* cited by examiner

*Primary Examiner*—Frank G. Font
*Assistant Examiner*—Andrew H. Lee
(74) *Attorney, Agent, or Firm*—Smyrski & Livesay, LLP

(57) ABSTRACT

A system and method for in-line inspection of specimens such as semiconductor wafers is provided. The system provides scanning of sections of specimens having predetermined standardized characteristics using a diffraction grating that widens and passes nth order (n>0) wave fronts to the specimen surface and a reflective surface for the transmitted light beam. Light energy is transmitted in a narrow swath across the portion of the surface having the standardized features. The wavefronts are combined using a second diffraction grating and passed to a camera system having a desired aspect ratio.

41 Claims, 7 Drawing Sheets

COPPER CMP FLATNESS MONITOR USING GRAZING INCIDENCE INTERFEROMETRY

This application is a continuation in part of U.S. patent application Ser. No. 08/930,378, entitled "Apparatus and Method for measuring Two opposite surfaces of a Body" filed on Sep. 24, 1997, now U.S. Pat. No. 6,100,977 which is the U.S. National Phase Application of EP 96/03381 filed on Aug. 1, 1996, the entirety of which is hereby incorporated by reference.

BACKGROUND OF THE INVENTION

1. Field of the Invention

The present invention relates generally to the art of optical inspection of specimens, such as semiconductor wafers and hard disk surfaces, and more specifically to a system for determining surface topographies in the nanometer range using optical techniques.

2. Description of the Related Art

Optical inspection techniques for specimens, such as semiconductor wafers, have assessed the relative flatness of specimen surfaces using various techniques. Surface flatness is a critical parameter used to determine the overall quality of a semiconductor wafer, and wafers having large irregular areas or small areas with radical height differences are undesirable.

For CMP (Chemical Mechanical Planarization) processed wafers, the starting material is a bare silicon wafer. Such a bare silicon wafer must be flat within certain tolerances regarding the height and spatial width of the flatness features.

Current tools available to measure wafer surface flatness include the "Magic Mirror" tool by Hologenix. The "Magic Mirror" operates by directing collimated light toward the wafer surface, wherein the collimated light source is angularly displaced from the wafer surface. The "Magic Mirror" system subsequently receives the reflected light, and the light received may be scattered toward or away from the detector. The "Magic Mirror" thereupon produces a two dimensional depiction of the surface of the observed semiconductor wafer, with associated light and/or dark areas depending on the type of defect. As can be appreciated, the "Magic Mirror" is a very subjective method of detecting surface contours. With different types of defects producing different optical effects, one cannot say for certain what type or size of defect is responsible for the bright or dark spot or area in the "Magic Mirror" depiction. Hence algorithms cannot conclusively provide areas of concern or threshold exceedance with reasonable degrees of certainty. The final two dimensional representation obtained from the "Magic Mirror" must be studied by an operator, and results depend on many uncontrollable factors.

Tools like the Magic Mirror can be used for flatness inspection of a bare wafer. However, for CMP processed wafer monitoring additional issues arise relating to the efficiency of the polishing, such as pitting and dishing of the patterned wafer surface. Magic mirror type tools are ineffective in addressing these types of anomalies.

A system addressing specimen flatness issues is the subject of current U.S. patent application Ser. No. 09/195,533, filed on Nov. 18, 1998, entitled "Detection System for Nanometer Scale Topographic Measurements of Reflective Surfaces" and developed by and assigned to KLA-Tencor Corporation, the assignee of the present application, provides a linear position array detector system which imparts light energy in a substantially normal orientation to a surface of a specimen, such as a semiconductor wafer, receives light energy from the specimen surface and monitors deviation of the retro beam from that expected. This system has particular advantages but requires a post processor to determine and fully compute the surface geometry for the entire specimen.

One device commonly used to measure the quality of the polishing of a CMP processed wafer is a profiler, much like a stylus on a record player, which directly contacts the semiconductor wafer surface. Such a system moves the semiconductor wafer and sensor relative to each other causing the sensor to linearly translate across the surface, thereby providing contact between the profiler and the entire surface. Movement of the profiler is recorded, and surface irregularities are detected when the profiler deflects beyond a threshold distance. The problems inherent in a profiler are at least twofold: first, a mechanical profiler contacting the wafer surface may itself produce surface irregularities beyond those present prior to the testing, and second, the time required to make accurate assessments of surface irregularities is extensive. For example, a full map of a single 200 mm wafer using a profiler may take between four and twelve hours.

A system is needed which diminishes the time required to perform surface scanning for contour differences and does not have the drawbacks inherent in the Magic mirror or profiler configurations. Further, it would be advantageous to provide a system which is less expensive than the KLA-Tencor normal incidence system and which can be used in examining less than the entire specimen surface quickly and efficiently. In particular, it would be desirable to have a system for determining specimen surface variations that would not risk damage to the specimen and would be quantitative in nature, thereby permitting contour quantification without ad hoc human review.

A further disadvantage of currently available flatness or contour measurement devices is that they stand separate from the production process and cannot be integrated into the process line. A developer or processing facility must first use the profiler or other device off line to inspect the surface of the specimen and subsequently place the specimen in the processing line for further inspection and processing.

It is therefore an object of the current invention to provide a system for determining the contours of portions of the surface of a specimen, such as a semiconductor wafer that can perform surface irregularity determination in less time and more cost effectively than systems previously known.

It is a further object of the current invention to provide a system for determining the contours of a wafer surface which does not increase the risk of damaging the wafer surface.

It is another object of the current invention to provide a system for inspecting the flatness or contour of a specimen that may be employed and integrated in the process line.

SUMMARY OF THE INVENTION

The present invention is a system and method for performing an in line inspection of a wafer or specimen using optical techniques. The wafer may be mounted in a vertical or horizontal orientation. Light energy is transmitted through a lens arrangement employing lenses having diameter smaller than the specimen, such as less than half the size of the specimen, arranged to cause light energy to strike the surface of the wafer and subsequently pass through a second collimating lens where detection and observation is performed.

The inventive system includes a low coherence light source that transmits light energy through a collimator, which collimates the light energy and directs the light energy to a diffraction grating. The diffraction grating splits the received beam into two separate first order beams. One first order beam is directed to the wafer surface, while the other beam is directed toward a flat reflective surface facing the wafer surface. Another diffraction grating is positioned to receive the two reflected first order beams and combine said beams toward a camera. The camera is specially designed to receive the signal provided and resolve the image of the wafer surface.

While the positive and negative first orders are preferably employed in the system as the test and reference arms, the gratings may be tilted to employ a different combination of orders as test and reference arms. Introduction of such a tilt may provide different combinations of orders used as test and reference arms, including zero order and higher order components. Further, the system may be arranged such that the angles of incidence on the surface vary, either by tilting the gratings or otherwise repositioning the components. Such variance may cause different orders of the components to strike the target surface and/or reference surface. Varying the incidence in this manner may in certain environments improve system resolution.

The light energy transmitted from the low coherence light source is dimensioned in conjunction with the collimator and diffraction grating to provide a narrow swath of light energy over a predetermined area of the wafer having a known pattern or set of characteristic features located thereon. Examination of a wafer to determine the overall quality of the wafer comprises a multiple point examination of the wafer, typically a five point inspection of known characteristic features on the specimen to determine the overall quality of the chemical-mechanical planarization process on the particular wafer. Further, the system provides for an areal examination of the entire field of view by rotation of the wafer in order to examine any location on the wafer. The system further has the ability to compare two or more locations on the wafer, such as the center of the wafer and the edge of the wafer, using a swath of light energy across the wafer surface. As wafer dimensions are on the order of 300 millimeters in diameter, the current system is directed to an examination of an area having dimension less than approximately 50 millimeters in width on the surface of the specimen. This less than approximately 50 millimeter wide area includes the salient features of the floor plan for a copper damascene CMP mask. The system disclosed herein transmits an approximately 50 millimeter wide swath or stripe of first order light energy onto the specimen and a similar swath onto the reflective surface facing the specimen. This narrow swath of light energy permits examination of particular features on the specimen and enables quantifying the quality of the CMP process without causing contact with the wafer and in a short amount of time. The present invention also permits a simple in-line examination procedure using a simple chuck and minimizes the need for ad hoc human review.

As may be appreciated, the current system transmits light energy at a relatively shallow angle, approximately 80 degrees from normal to the surface of the specimen, and thus the area of the wafer illuminated is on the order of six times larger than the dimension of the transmitted light energy. As a result of this 1:6 dimensioning, an improved camera arrangement is employed to resolve the image and accurately examine the data.

In order to measure certain anomalies created by the CMP process, the system must be capable of micrometer range spatial resolution. Thus the camera arrangement has zoom capability to accurately measure these imperfections.

These and other objects and advantages of the present invention will become apparent to those skilled in the art from the following detailed description of the invention and the accompanying drawings.

DETAILED DESCRIPTION OF THE INVENTION

For a full understanding of the inventive system disclosed herein, it must first be appreciated that a specimen such as a semiconductor wafer may undergo a variety of processes and/or evaluations to determine the quality of the circuit located thereon. In most circumstances, a complete scan of the specimen is required to determine the quality of the specimen and the processing which has occurred. In certain limited circumstances, a subset of the entire wafer or specimen may be advantageous to determine the general quality of the wafer as opposed to the detailed quality of the individual circuits etched thereon. For purposes of this invention, the initial general scan comprising an evaluation of a subset of the specimen surface is differentiated from a complete scan of the entire surface of the specimen. The present invention is primarily directed to the former rather than the latter.

Figure 1:
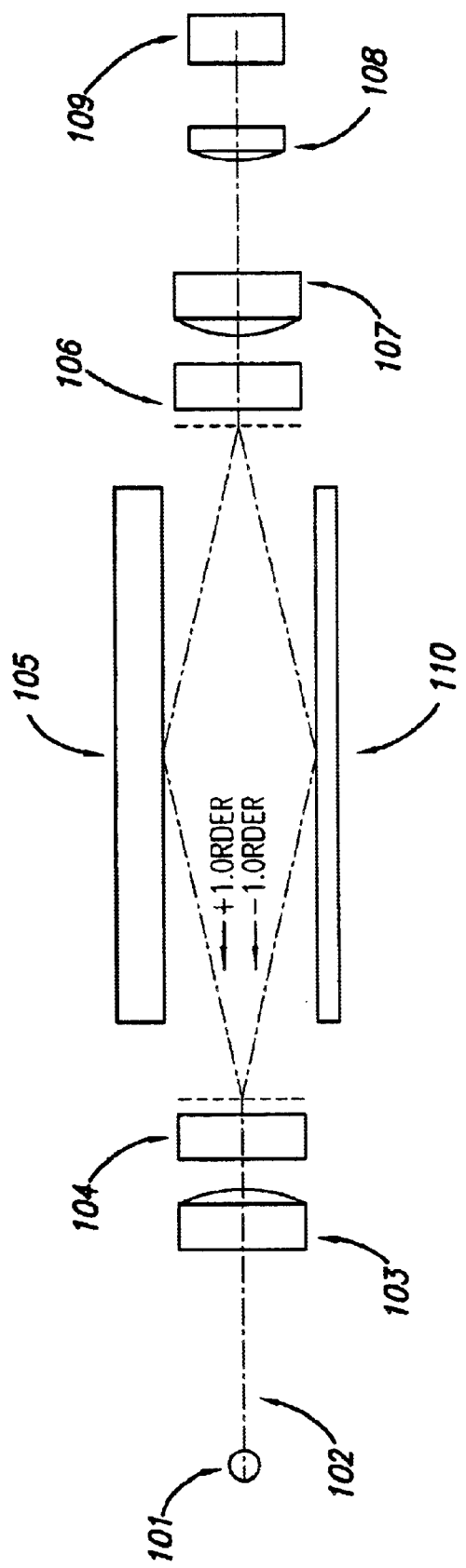
FIG. 1 illustrates a conceptual drawing of the current invention.

FIG. 1 illustrates a conceptual drawing of the current invention. As shown in FIG. 1, a low coherence light source 101 is employed to generate a low coherence light beam 102. The low coherence light beam strikes a collimator 103 which collimates the light beam and transmits light energy to a first transmission grating 104. First transmission grating 104 splits the received light energy into multiple order components, including but not limited to a zero order component and at least one first order component. The zero order component may optionally be blocked in the arrangement shown in FIG. 1. As shown in FIG. 1, first transmission grating 104 generates a positive and negative first order component that is directed in a preferential orientation toward a reference mirror 105 and the wafer or specimen 110. The first order components strike the reference mirror 105 and the specimen 110 and are directed toward second transmission grating 106, which combines the two first order components and directs the resultant light energy toward decollimator 107. Decollimator 107 collects the light energy and decollimates the energy. Energy transmitted by decollimator 107 is received by camera optics 108 and transmitted to imaging sensor 109, which may be a CCD.

While the positive and negative first order components are preferably used as the test and reference arms of the interferometer, and the zero order blocked or optimized for zero intensity, the system may be configured or operated such that a tilt of the gratings 104 and 106 causes varying orders of the light energy to strike the target surface and/or the reference surface. Tilting the gratings 104 and 106 may in certain environments provide enhanced imaging and resolution. Alternately, the system may be varied to provide different angles of incidence on the reference surface or the target surface. Altered angles of incidence may provide enhanced resolution in certain conditions, and may be used to cause zero, first, or higher order light components to strike the reference or target surface.

The planarization process for a Copper CMP (Chemical Mechanical Planarization) processed wafer requires first subjecting an unfinished wafer to the process and subsequently examining the wafer for defects. Different effects from the CMP process provide different anomalies on the surface of the specimen. For example, certain processes can cause global planarization anomalies, with differences in surface height measurable only by determining heights over large areas of the wafer. Smaller sections of the specimen may suffer from field local erosion, wherein small areas are lower than other proximate areas. Finally, lines formed of metal can wear away during the CMP process, resulting in local line dishing and requiring higher spatial resolution to determine the defects.

In this environment, it is advantageous to examine less than the entire surface of the wafer to determine the anomalies present on a particular wafer that result from the CMP process. Typical scanning of the surface involves a multiple point inspection, typically a five point inspection, of the surface of the specimen to determine as many anomalies as possible with the least amount of points examined as possible.

In operation, the device of FIG. 1 measures a single side of the specimen 110. The aperture of the low coherence light source is reduced to smaller than 50 by 50 millimeters to permit measurement of a 300 by less than 50 millimeter striped area on a 300 millimeter wafer. This less than 50 millimeter wide area covers an area large enough toperform a scan of a Copper Damascene CMP mask, as well as one or more masks at different locations on the wafer. By rotating the CMP processed wafer, the use of the swath of light energy described herein to illuminate the specimen from edge to edge. The ability to examine the wafer from at least the center of the wafer to the edge thereof permits examination of any point on the wafer by simply rotating the wafer such that the point of interest is within the swath of light energy. Rotation permits a comparison between two or more points on the surface of the CMP mask.

Figure 2:
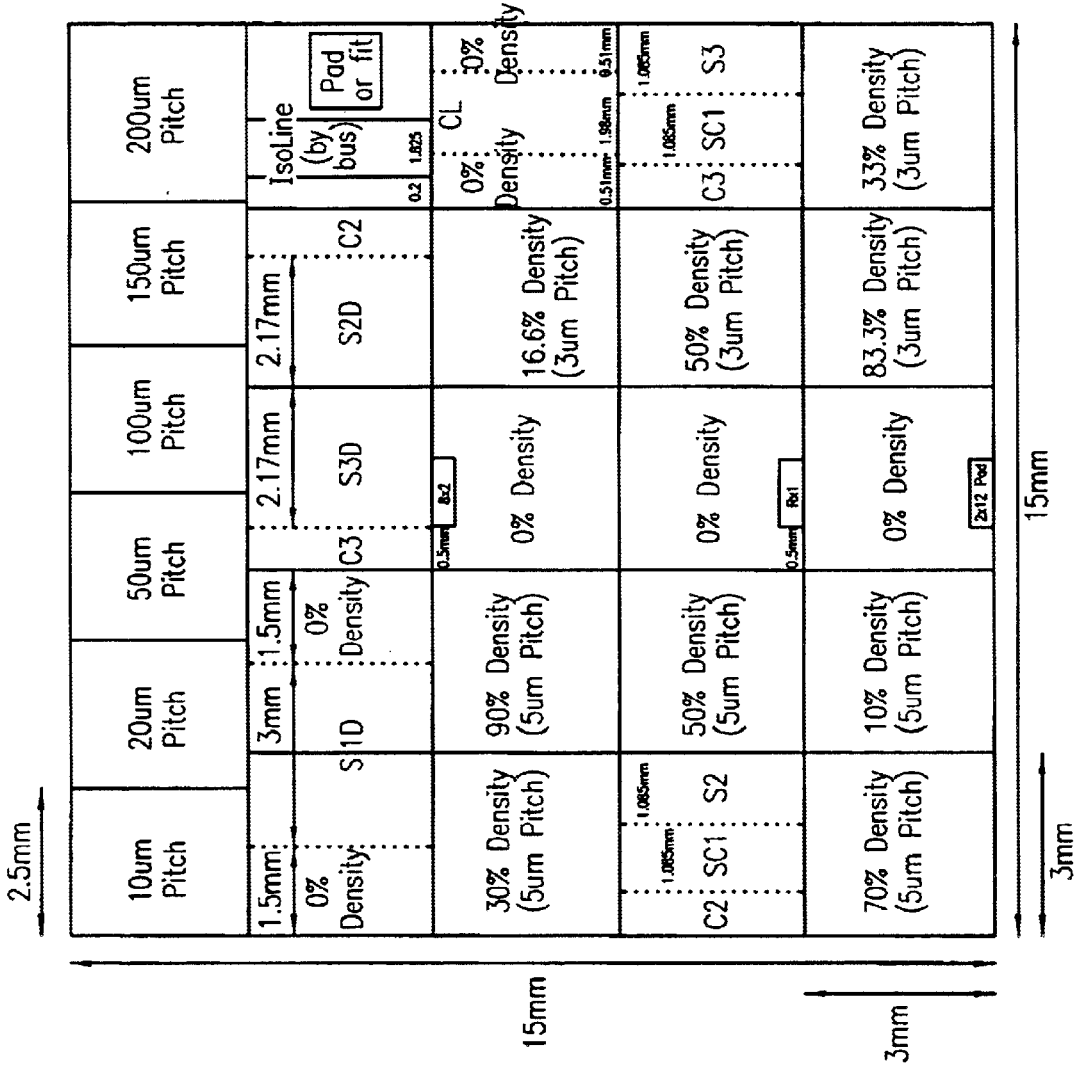
FIG. 2 presents the floor plan for a typical copper damascene CMP mask, including the standardized topography for each of the sections of a predetermined section of the mask.

A floor plan for a typical Copper Damascene CMP mask is presented in FIG. 2. As shown in FIG. 2, various "pitch" sections, or blocks, of the mask are filled with vertical lines ranging from 10 micrometers to 200 micrometers at a fixed density of 50 per cent. In the "density" blocks, each block has a specified density with vertical lines at fixed pitches of 3 micrometers and 5 micrometers. Density is equal to copper linewidth divided by the pitch. The three blocks S1D, S2D, and S3D provide a continuity test on different linewidths having fixed linespace. Further, the S1D, S2D, and S3D blocks serve as density blocks for minimum and fine pitch values, i.e. 0.35/0.35. The S2 and S3 blocks are employed for a continuity test. SC1 is a combined serpentine and comb structure. C2 and C3 are comb-like structures for non-shorting (among different copper lines) testing. Each structure is 0.775 millimeters in width.

The purpose of the floor plan of FIG. 2 is to provide a standard area wherein the effects of global planarization, local erosion, and local dishing may be assessed. The varying pitches, wire densities, linewidths, and line spaces provide a variety of situations a CMP processed wafer may encounter. Thus, observation of a floor plan as shown in FIG. 2 presents a significant baseline for determining the errors present on the entire wafer due to the CMP process.

As shown in FIG. 2, a typical floor plan is approximately a 15 millimeter square, with sections ranging up to 3 millimeters square. These dimensions afford a baseline for examination by inspecting a portion of the wafer surface rather than the entire surface. Hence the current device affords scanning of the wafer including a scan of the copper CMP floor plan of FIG. 2. From the system of FIG. 1, the light energy transmitted onto the surface of the specimen is an approximately 300 millimeter by less than 50 millimeter swath, an area large enough to characterize and monitor the effects of the planarization process. A smaller area than 300 by 50 millimeters may be sufficient, such as one covering the floor plan of FIG. 2, i.e. a stripe or swath in excess of 15 millimeters in width. Using the system illustrated in FIG. 1, the stripe is measured in a single step (imaging) and no scanning is required. The specimen may be oriented in either a vertical or a horizontal manner.

In operation, the wafer or specimen is held either vertically or horizontally during measurement. The diverging light of the low coherence light source is collimated and diffracted by the transmission grating into plus and minus first order components, among other components. One order illuminates the specimen, while the other order illuminates a plano reference mirror substantially parallel to the wafer surface and at a distance to the wafer which provides a common path length for both the positive and negative first orders. The suggested angle of incidence is approximately 80 degrees on both the wafer surface and reference surface, where 80 degrees is measured from normal to the wafer or reference surface down to the light beam. Other grazing angles may be employed while remaining within the scope of this invention.

After reflecting both orders from the surfaces, the two first order components are recombined to the zero order by the second transmission grating. The decollimator and lens system image the swath or stripe observed on a high resolution CCD imaging sensor. The system employs phase shifting to acquire height information, and digital image processing to calculate phase information. The system unwraps the phase and filters the resultant height information from the wafer topography to evaluate local and global flatness uniformity for different spatial wavelengths. In this configuration, grazing incidence enlarges the dynamic measuring range necessary to measure large areas on bowed wafers. Low coherence reduces noise problems from multiple reflected orders due to different diffraction patterns on wafers. The second diffraction grating used to recombine the positive and negative first order components also acts to filter out the pattern generated diffraction orders.

In the system illustrated in FIG. 1, reference surfaces and specimen surfaces are positioned such that the reference wave fronts and specimen wave fronts travel the same path length. Phase shifting may be established by moving the reference surfaces, the diffraction gratings, or the light source. Thus the overall effect of the system illustrated in FIG. 1 is to decrease the required spatial coherence between the reference wave fronts and the specimen wave fronts.

Figure 3:
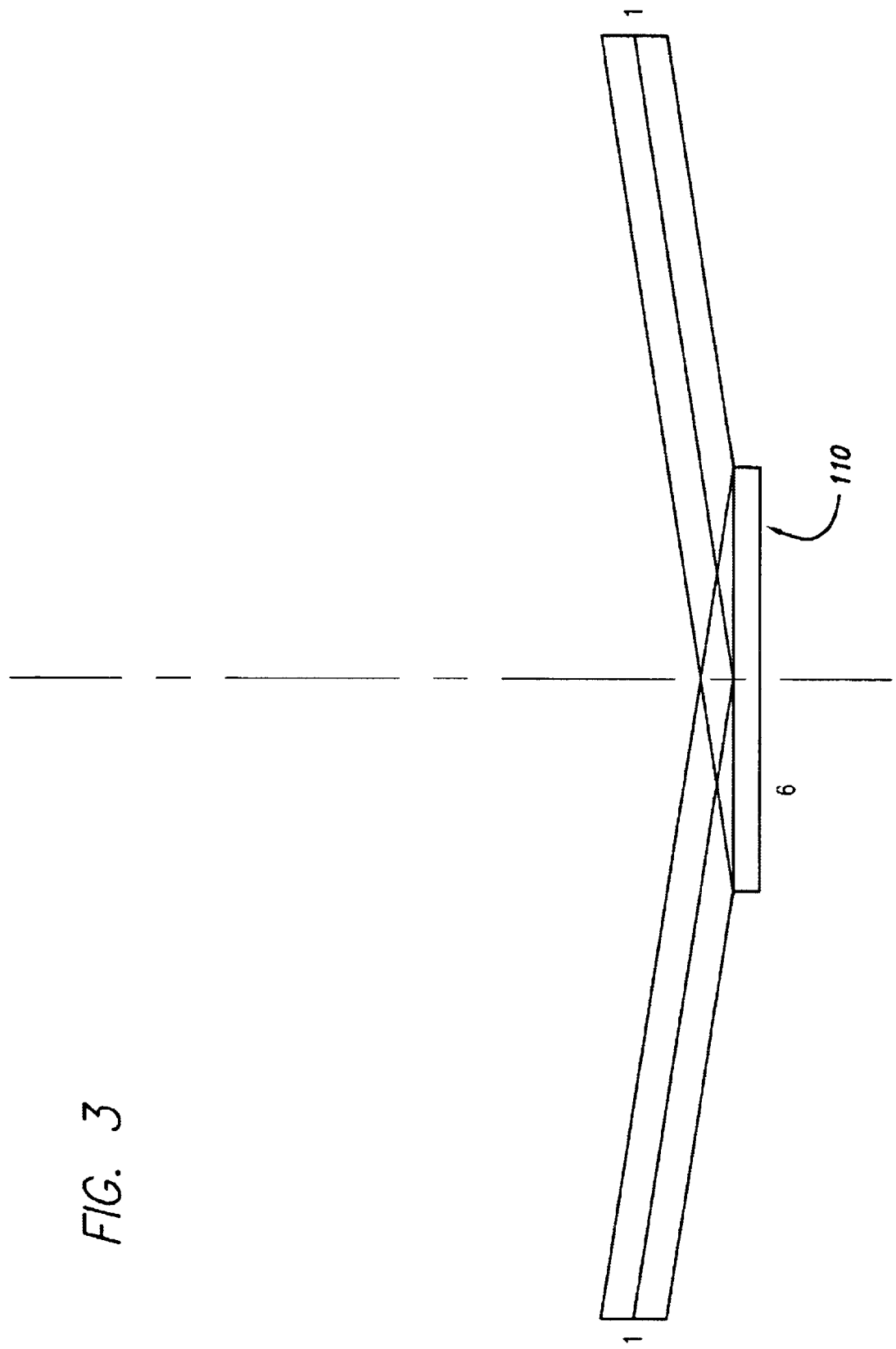
FIG. 3 illustrates the general concept of the 6:1 or 1:6 aspect ratio of the transmitted and received light energy to and from the surface of the specimen.

The camera system or camera optics 108 is an anamorphic imaging system having an aspect ratio of on the order of 2:1. In essence, the wafer in the configuration illustrated optically appears as a tilted object, and in the arrangement shown has an elliptical projection ratio of approximately 6:1. The camera system used should preferably resolve this elliptical projection ratio into an image having an aspect ratio closer to 1:1. Maintaining the aspect ratio of 6:1 can prevent detection of relatively significant magnitude. An illustration of the 6:1 relationship in the projection of the swath or stripe of light energy is presented in FIG. 3, wherein specimen or wafer 110 receives and reflects light energy.

Figure 4:
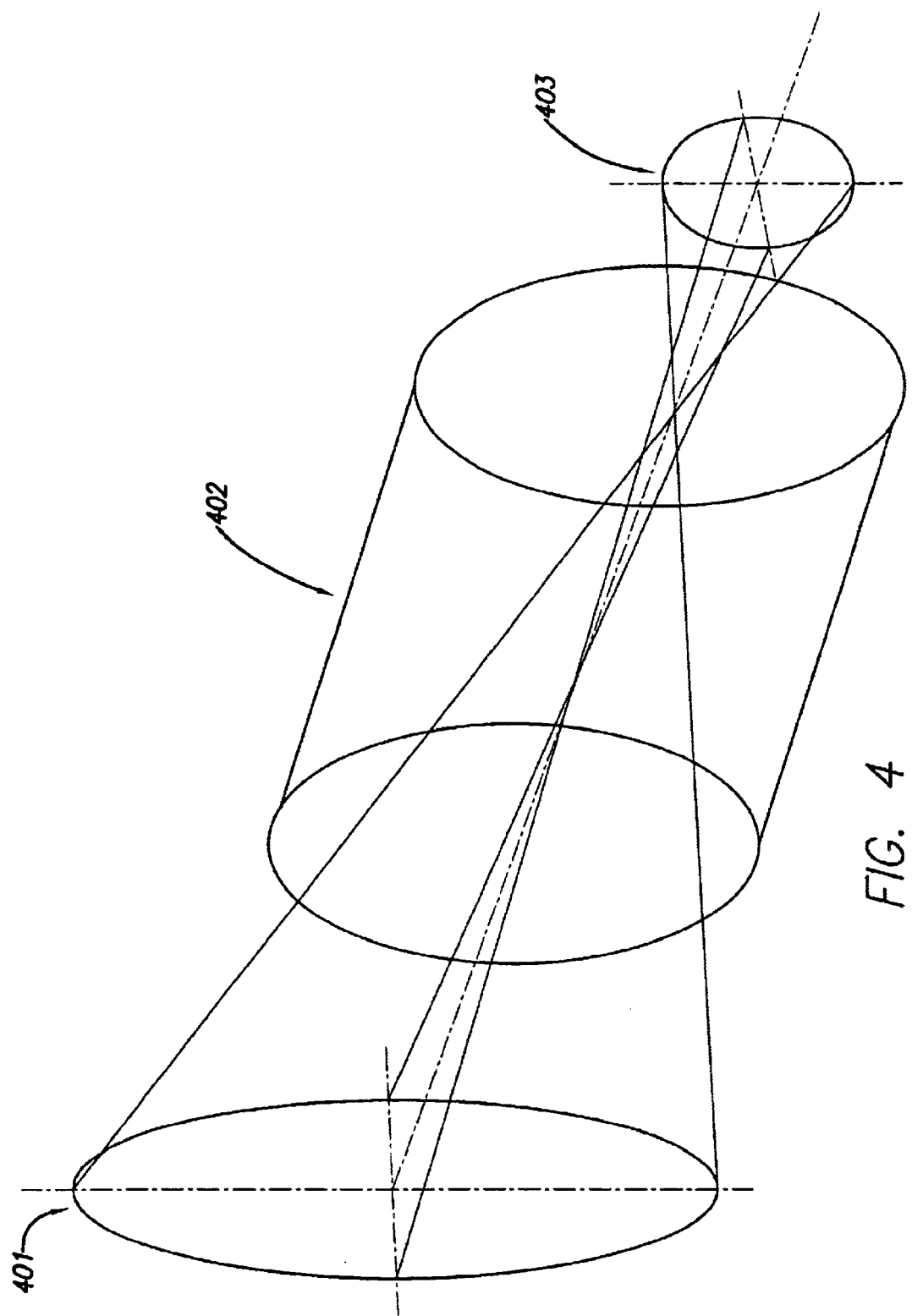
FIG. 4 presents the camera system or camera optics employed in the current invention.

The overall configuration of the anamorphic imaging system used in the system disclosed herein is shown in FIG. 4. From FIG. 4, the projection of the image has an elliptical aspect ratio of 6:1. The anamorphic imaging system 401 receives the elliptical image 402 and conveys the image to a viewing location, such as a CCD (Charged Coupled Device) such that the received image 403 has an aspect ratio of 2:1. This ratio provides the maximum utilization of a square image when imaging each of the wafer stitching regions. Different anamorphic imaging arrangements may be employed while still within the scope of the current invention; the intention of the anamorphic system and function thereof is to provide a sufficient image based on the surfaces being scanned and the size and quality of defects expected, as well as the resolution capability of the overall system.

In order to measure certain anomalies created by the CMP process, such as dishing, the system has micrometer range spatial resolution. Dishing anomalies are measured over roughly two millimeters within multiple fields of varying line densities, thus requiring this micrometer range spatial resolution. The camera system 108 therefore has zoom capability to accurately measure these dishing attributes. Using a zoom capability and therefore reducing the field of view require an x/y translation of the specimen, an x/y translation of the interferometer, or an x/y translation of the imaging system. This translation of components permits enhanced dishing measurement using the zoom capability of the camera system 108. The wafer is translated by mechanical or automated means known to those of skill in the art, while the interferometer and imaging system translation is performed by releasing, moving, and fixing the position of the appropriate components, or by other translation procedures and devices known to those skilled in the art.

Figure 5:
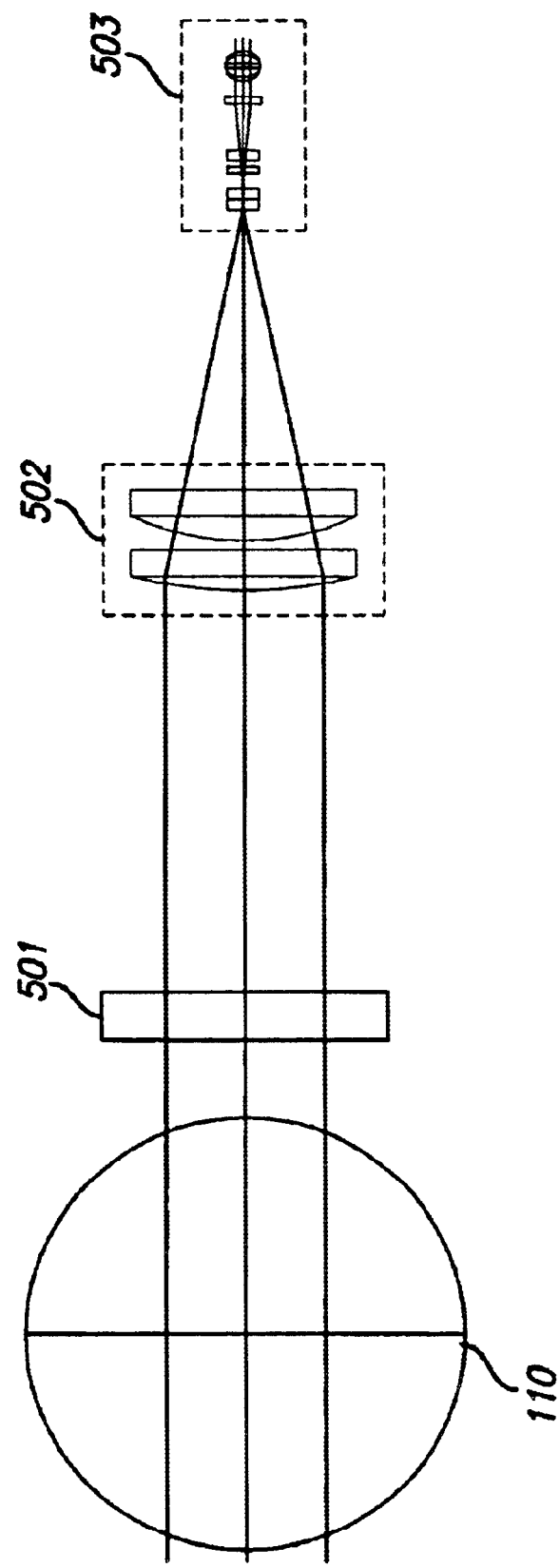
FIG. 5 is a simplified drawing of the system from the wafer to the camera arrangement.

A simplified drawing of the system from the wafer to the camera arrangement is presented in FIG. 5. FIG. 5 is not to scale. From FIG. 5, wafer or specimen 110 reflects the light energy toward second diffraction grating 501, which passes light to collimator 502 and to a camera arrangement 503. Camera arrangement 503 comprises seven imaging lenses used to resolve the 6:1 image received into a 2:1 image for transmission to imaging sensor or CCD 109. Any lensing arrangement capable of producing this function is acceptable, and the camera arrangement 503 is therefore not limited to that illustrated in FIG. 5.

Figure 6:
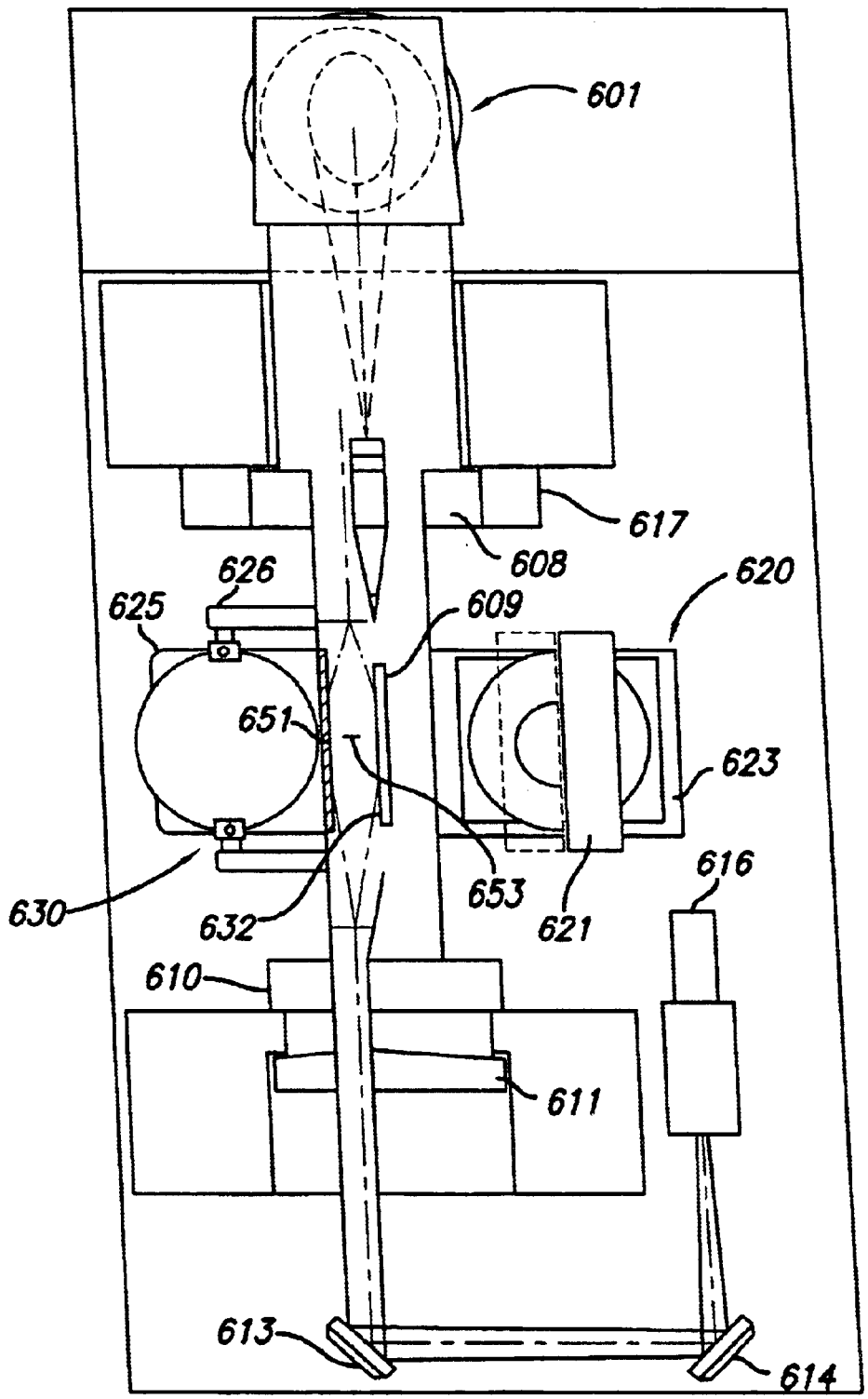
FIG. 6 presents a conceptual schematic representation of the components and optics necessary to perform the inventive imaging of a predetermined portion of a semiconductor wafer.
Figure 7:
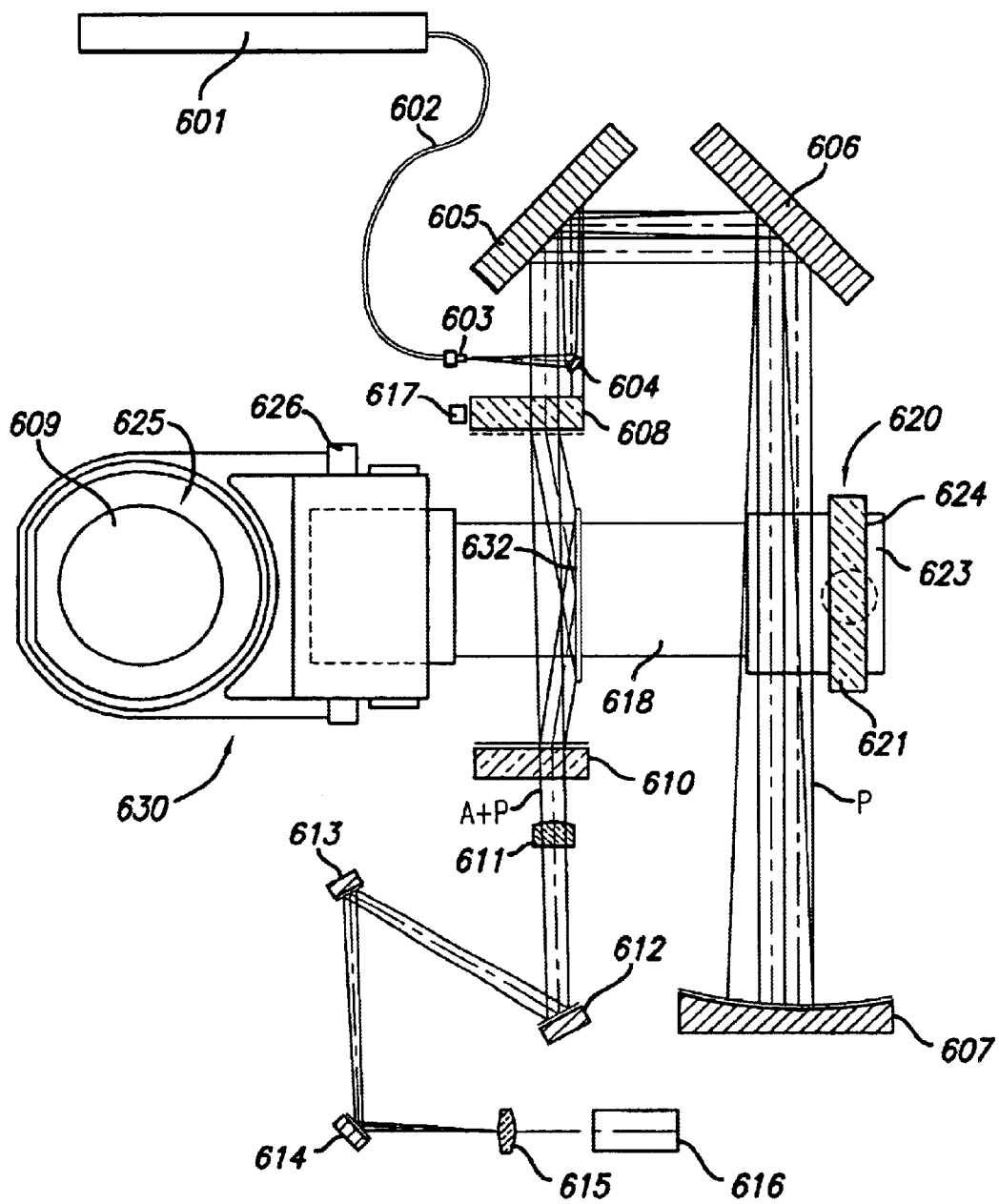
FIG. 7 is a top view of the components of FIG. 4 and the optics showing the path of light energy.

Imaging of the specimen is generally performed in accordance with PCT Application PCT/EP/03881 to Dieter Mueller, currently assigned to the KLA-Tencor Corporation, the assignee of the current application. The entirety of PCT/EP/03881 is incorporated herein by reference. This imaging arrangement is illustrated in FIGS. 6 and 7, and is employed in conjunction with the arrangement illustrated and described with respect to FIG. 1 herein. FIGS. 6 and 7, as well as FIG. 1, are not to scale. As shown in FIGS. 6 and 7, the light energy directing apparatus employed in the current invention comprises a light source in the form of a low coherence laser 601. The light emitted from the laser 601 is conducted through a beam waveguide 602. The light produced by the laser 601 emerges at an end 603 of the beam waveguides 602 so that the end 603 acts as a punctual light source. The emerging light strikes a deviation mirror 604 wherefrom it is redirected onto a collimation mirror 607 in the form of a parabolic mirror by two further deviation mirrors 605 and 606. Deviation mirrors 605 and 606 are oriented at an angle of 90° relative to each other. The parallel light beam P reflected from the parabolic mirror 607 reaches a beam splitter 608 through the two deviation mirrors 605 and 606.

The beam splitter 608 is formed as a first diffraction grating. The beam splitter 608 as shown is arranged in the apparatus in a vertical direction and the parallel light beam P strikes the diffraction grating in a perpendicular direction. As may be appreciated by those of skill in the art, the specimen may be oriented in the horizontal direction, thereby requiring a simple re-orientation of the optical components.

A beam collector 610 in the form of a second diffraction grating is disposed from the first diffraction grating 608 and parallel thereto. Behind the beam collector 610 is located a decollimation lens and the light beam leaving the decollimation lens is deflected and focused onto a CCD camera 616, through deviation mirrors 612, 613, and 614, and through lens 615.

In the arrangement shown, the beam splitter 608 is supported transversely to the optical axis and further comprises a piezoelectric actuating element 617 for shifting the phase of the parallel light beam P by displacing the diffraction grating.

As noted, in order to provide for inspection of a portion of the wafer surface in-line during the overall specimen inspection process, the orientation of the system may differ from that shown in FIGS. 6 and 7. For example, it may be preferable to provide a horizontal orientation of the wafer to reduce the need for human interaction. Alternately, as shown in FIGS. 6 and 7, the specimen may be vertically oriented. In either orientation, the reference mirror 105 of FIG. 1 or 651 of FIG. 6 must be provided substantially parallel to the wafer surface and providing a common path length between the transmission gratings.

To facilitate the inspection, a holding device 630 may be provided between the first diffraction grating and the second diffraction grating. A wafer or specimen 609 to be measured may be held on the holding device 630 such that both plane surfaces 631 and 632 are arranged in vertical direction parallel to the light beam P. The wafer 609 is supported by the support post substantially at its vertical edge 633 only so that the surface 632 is not substantially contacted by the support post and are freely accessible to the interferometric measurement.

Moreover, an optional receiving device (630, 625) may be provided for measuring the wafer 609. This receiving device (630, 625) provides for arrangement of the wafer in line in the system. The wafer can be inserted into the receiving device in a horizontal position. By means of a tilting device 626 the wafer 609 may be tilted from its horizontal position into the vertical measuring position, and the wafer 609 may be transferred, by means of a positionable traveller into the light path between the first diffraction grating and the second diffraction grating so that the surfaces 609 and 632 to be measured are aligned substantially parallel to the undiffracted light beam P and in a substantially vertical direction.

In operation the wafer or specimen 609 to be measured may be first inserted into the wafer receiving device 625. The surfaces 631 and 632 are horizontally arranged. By means of the tilting device and of the traveller 619 the wafer to be measured is brought into the holding device 630 where it is arranged so that the specimen 609 is vertically oriented. A diffraction of the parallel light beam P striking the first diffraction grating 608 of the beam splitter produces partial light beam or narrow swath or stripe A, whereby the first order component of the partial light beam A having a positive diffraction angle strikes one surface 632 of the wafer 609 and is reflected. The first order component of partial light beam A strikes the reflective surface or flat 651. The 0-th diffraction order of the parallel light beam P passes through the first diffraction grating 608 and is not reflected at the surface 632 of the wafer 609. This partial light beam P serves as a reference beam for interference with the reflected wave fronts of beam A. The 0-th order beam is preferably blocked by blocking surface 653. In the second diffraction grating 610, the beam collector and the reflected first order components of partial light beam A is combined with the reference beam P and focused, in the form of partial light beam A+P onto the focal planes of the CCD camera 616 through decollimation lens 611 and deviation mirrors 612, 613 and 614 as well as positive lens 615.

During the exposure of the surfaces the phase of the parallel light beam P is repeatedly shifted by multiples of 90° and 120° by displacing the diffraction grating. This produces phase shifted interference patterns. The defined shift of the interference phase produced by the phase shifter 617 is evaluated to determine whether there is a protuberance or a depression in the measured surface 631.

It should be noted that in the manner illustrated in the preferred embodiment and in general the wafer specimen is able to be rotated such that data may be acquired for any location on the specimen. While one particular wafer holding apparatus is illustrated, it is to be understood that any type of wafer holding device is generally acceptable that provides for relatively simple rotation and data acquisition. Using such a wafer holding apparatus, the swath of light can cover and examine a strip extending at least from the center of the specimen to the edge of the specimen. Use of the term "center" means a point approximately central to a generally round specimen, or at a non-edge point in a non-circular specimen. The system and method disclosed herein provide for examination of global planarization, erosion, and dishing on the CMP processed wafer surface. The system and method can be integrated into the CMP process line, and various CMP processed wafers are successfully examined using the invention described herein, including but not limited to unpatterned wafers with film, patterned test wafer with test mask, patterned production wafer with combination of product and test mask, and patterned production wafers free of test masks.

While the invention has been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. A system for performing a scan of a portion of a specimen surface, comprising:
   a collimator for collimating light energy received from a low coherence light energy generating device;
   a first diffraction grating combining light energy transmitted from said collimator and passing nonzero order light energy toward said specimen;
   a reflective surface for receiving predetermined order light energy from said diffraction grating;
   a second diffraction grating for receiving light reflected from said specimen and from said reflective surface; and
   a collimator for receiving light energy from said second diffraction grating;
   wherein said first diffraction grating passes light energy only over a portion of the specimen surface having predetermined standardized characteristics, said portion comprising less than half of the specimen surface, and said predetermined standardized characteristics comprising a set of physical attributes varying between specific sections on the specimen surface.

2. The system of claim 1, wherein said predetermined order light energy is first order light energy.

3. The system of claim 2, wherein said reflective surface receives nonzero order light energy passed from said diffraction grating.

4. The system of claim 2, further comprising a blocking element for blocking passage of zero order light energy received from said first diffraction grating.

5. The system of claim 1, wherein the camera converts an elliptical image of said portion of said specimen into an image having an aspect ratio closer to 1:1.

6. The system of claim 1, wherein each receiving collimator comprises at least one lens.

7. The system of claim 2, wherein nonzero order light energy passes from said first diffraction grating toward said reflective surface and said specimen.

8. The system of claim 2, wherein said first diffraction grating is optimized for zero intensity of its zero order.

9. The system of claim 2, further comprising means for rotating said specimen surface to expose alternate portions of said surface to said light energy.

10. The system of claim 1, wherein said first diffraction grating passes light energy over a portion of the specimen surface extending at least from a center of the specimen surface to an edge of the specimen surface.

11. The system of claim 1, wherein said system performs the scan of the portion of the specimen surface to assess at least one from a group comprising global planarization, erosion, and dishing.

12. The system of claim 1, wherein said specimen comprises a CMP processed wafer, and said specimen comprises one from the group including:
   (a) unpatterned wafers with film;
   (b) patterned test wafer with test mask;
   (c) patterned production wafer with combination of product and test mask; and
   (d) patterned production wafers free of test masks.

13. The system of claim 1, wherein said system is integrated into a CMP processed wafer production line.

14. The system of claim 1, further comprising a camera for receiving light energy from the receiving collimator, wherein the camera has zoom capabilities.

15. The system of claim 14, further comprising at least one translation means from the following:

(a) wafer translation means;

(b) interferometer translation means; and (c) imaging system translation means;

wherein the translation means reduce the field of view generated by the zoom capabilities of the camera.

16. The system of claim 1, wherein the set of attributes varied comprises at least one from a group comprising surface pitch, wire density, linewidth, and line spaces.

17. A method for inspecting a portion of a surface of a specimen, comprising:

transmitting light energy toward said specimen;

diffracting said light energy into predetermined order light energy;

directing said diffracted light energy toward a predetermined portion of said specimen surface having predetermined standardized characteristics and simultaneously toward a reflective surface mounted substantially parallel to said specimen surface, wherein said predetermined portion comprises less than half of the specimen surface;

receiving predetermined order light energy reflected from said specimen and said reflective surface and combining the received light energy; and directing said light energy to a light receiving device;

wherein said predetermined standardized characteristics comprise known physical variations between sections on the specimen surface.

18. The method of claim 17, wherein said predetermined order light energy comprises nonzero order light energy.

19. The method of claim 18, wherein said diffracting step comprises diffracting for zero intensity of the zero order of the light energy received.

20. The method of claim 17, further comprising the step of initially calibrating the system prior to said transmitting step.

21. The method of claim 17, wherein said light energy forms an image, and said directing step comprises altering the image aspect ratio.

22. The method of claim 17, wherein said method provides light energy to a strip extending from at least a center of said specimen to an edge of said specimen.

23. The method of claim 17, wherein said method addresses and assesses at least one of the anomalies from a group comprising global planarization, erosion, and dishing.

24. The method of claim 17, wherein said method is integrated into a CMP process line.

25. The method of claim 17, wherein said specimen comprises a CMP processed wafer, and said specimen comprises one from the group including:

(a) unpatterned wafers with film;

(b) patterned test wafer with test mask;

(c) patterned production wafer with combination of product and test mask; and (d) patterned production wafers free of test masks.

26. The method of claim 17, wherein said light receiving device comprises a camera having zoom capabilities.

27. The method of claim 25, further comprising translating components to provide a reduced field of view when using the camera zoom capabilities.

28. The method of claim 17, wherein said known physical variations on the surface comprise at least one from a group comprising surface pitch variations, wire density variations, linewidth variations, and line space variations.

29. A method for inspecting a surface of a specimen, said surface having a surface area, comprising:

disposing a swath of nonzero order light energy having approximate predetermined dimension across said surface of said specimen while simultaneously transmitting predetermined order light energy toward a reflective surface, said swath covering less than approximately half of the surface area of the specimen; and combining light energy received from said surface and said reflective surface;

wherein said disposing comprises disposing light energy to a portion of said surface having predetermined standardized characteristics, and said predetermined standardized characteristics comprising at least one from a group comprising surface pitch variations, wire density variations, linewidth variations, and line space variations.

30. The method of claim 29, wherein said predetermined order light energy comprises nonzero order light energy.

31. The method of claim 29, further comprising collimating light energy prior to said disposing step.

32. The method of claim 30, further comprising diffracting light energy transmitted from said collimating step and passing diffracted nonzero order light energy toward said specimen.

33. The method of claim 32, further comprising diffracting and collimating light received from said combining step.

34. The method of claim 33, further comprising blocking passage of zero order light energy received from said diffracting step.

35. The method of claim 29, further comprising converting an image of said portion of said specimen into an image having an aspect ratio closer to 1:1.

36. The method of claim 30, wherein said collimating step employs at least one lens.

37. The method of claim 30, wherein said diffracting step is optimized for zero intensity of the zero order of the light energy.

38. The method of claim 29, wherein said method provides light energy to a strip extending from at least a center of said specimen to an edge of said specimen.

39. The method of claim 29, wherein said method addresses and assesses at least one of the anomalies from a group comprising global planarization, erosion, and dishing.

40. The method of claim 29, wherein said method is integrated into a CMP process line.

41. The method of claim 29, wherein said specimen comprises a CMP processed wafer, and said specimen comprises one from the group including:

(a) unpatterned wafers with film;

(b) patterned test wafer with test mask;

(c) patterned production wafer with combination of product and test mask; and (d) patterned production wafers free of test masks.

* * * * *